(12) United States Patent
Popescu

(10) Patent No.: US 12,727,779 B2
(45) Date of Patent: Sep. 8, 2026

(54) TECHNIQUES IMPLEMENTING MRI FOR CANCER CLASSIFICATION

(71) Applicant: Siemens Healthcare GmbH, Erlangen (DE)

(72) Inventor: Stefan Popescu, Erlangen (DE)

(73) Assignee: Siemens Healthineers AG, Erlangen (DE)

( * ) Notice: Subject to any disclaimer, the term of this patent is extended or adjusted under 35 U.S.C. 154(b) by 484 days.

(21) Appl. No.: 18/220,914

(22) Filed: Jul. 12, 2023

(65) Prior Publication Data

US 2024/0016407 A1 Jan. 18, 2024

Related U.S. Application Data

(60) Provisional application No. 63/388,351, filed on Jul. 12, 2022.

(51) Int. Cl.
*A61B 5/055* (2006.01)
*G06T 7/00* (2017.01)

(52) U.S. Cl.
CPC ............ *A61B 5/055* (2013.01); *G06T 7/0012* (2013.01); *G06T 2207/10088* (2013.01); *G06T 2207/20081* (2013.01); *G06T 2207/30096* (2013.01)

(58) Field of Classification Search
CPC ..... A61B 5/055; A61B 5/7267; G06T 7/0012; G06T 2207/10088; G06T 2207/20081; G06T 2207/30096; G01R 33/5608; G01R 33/56
See application file for complete search history.

(56) References Cited

U.S. PATENT DOCUMENTS

| | | | | |
|---|---|---|---|---|
| 7,839,147 | B2 | 11/2010 | Katscher et al. | |
| 9,645,214 | B2 | 5/2017 | Hancu et al. | |
| 9,903,921 | B2 | 2/2018 | Sodickson et al. | |
| 10,302,713 | B2 | 5/2019 | Popescu | |
| 10,338,183 | B2 | 7/2019 | Popescu | |
| 2009/0267602 | A1 * | 10/2009 | Hardy | G01R 33/4836 324/309 |
| 2012/0150458 | A1 * | 6/2012 | Sodickson | G01R 33/288 702/57 |
| 2020/0167975 | A1 | 5/2020 | Popescu | |
| 2023/0152404 | A1 * | 5/2023 | Saha | A61B 5/055 600/410 |

OTHER PUBLICATIONS

Scalpi, Michele ("Biparametric MRI of the prostate" Turkish Journal of Urology) (Year: 2017).*
Nickneyad MT et al.:"Breast Imaging-Reporting and Data System (BI-RADS)," Radiopaedia, last revised Aug. 21, 2022, https://radiopaedia.org/articles/breast-imaging-reporting-and-data-system-bi-rads?lang=us.
Weerakkody Y, "PI-RADS, Prostate Imaging-Reporting and Data System (PI-RADS)," Radiopaedia, last revised Feb. 18, 2022 https://radiopaedia.org/articles/prostate-imaging-reporting-and-data-system-pi-rads-1#:~:text=PI%2DRADS%201%3A%20very%20low,is%20likely%20to%20be%20present).
IT IS Foundation "Tissue Property," https://itis.swiss/virtual-population/tissue-properties/database/dielectric-properties/.

* cited by examiner

*Primary Examiner* — Molly Wilburn
(74) *Attorney, Agent, or Firm* — Banner & Witcoff, Ltd.

(57) ABSTRACT

Techniques are described for classifying tissue based on magnetic resonance image data, comprising. These may include acquiring magnetic resonance image data of a tissue region, detecting the tissue region contained within the magnetic resonance image data, acquiring information on an electrical property of the tissue region, and classifying the tissue region based upon the information on the electrical property of the tissue region.

20 Claims, 9 Drawing Sheets

$C_j$
phase
encoding
direction
k-lines
k-lines
frequency
encoding
pattern
$V_i$
Frequency
encoding
direction
θ

Terminal
13
14
5
21
15
16
S
Main Field Magnet
1
Shim Coils
2
Gradient Coils
3
0
RF Antenna
4
M
16
23
Image
Computer
10
6
Diplexer
7
RF Amp
20
17
22
8
8'
System
Computer
11
ADC
Recep.
Channel
19
9
DAC
Trans.
Channel
Synthesizer
18
12
24
RF System
RF
Amp
$G_x$
$G_y$
$G_z$
DAC
DAC
DAC
Shim
Coils
Supply
30
Sequence
Controller 410
Acquiring magnetic resonance image data of a tissue region
401
Detecting a tissue region contained within the magnetic resonance image data
402
Acquiring information on an electrical property of the tissue region
403
Generating a synthetic image
405
Classifying the tissue region based upon the synthetic image and the electrical properties of the tissue region
404

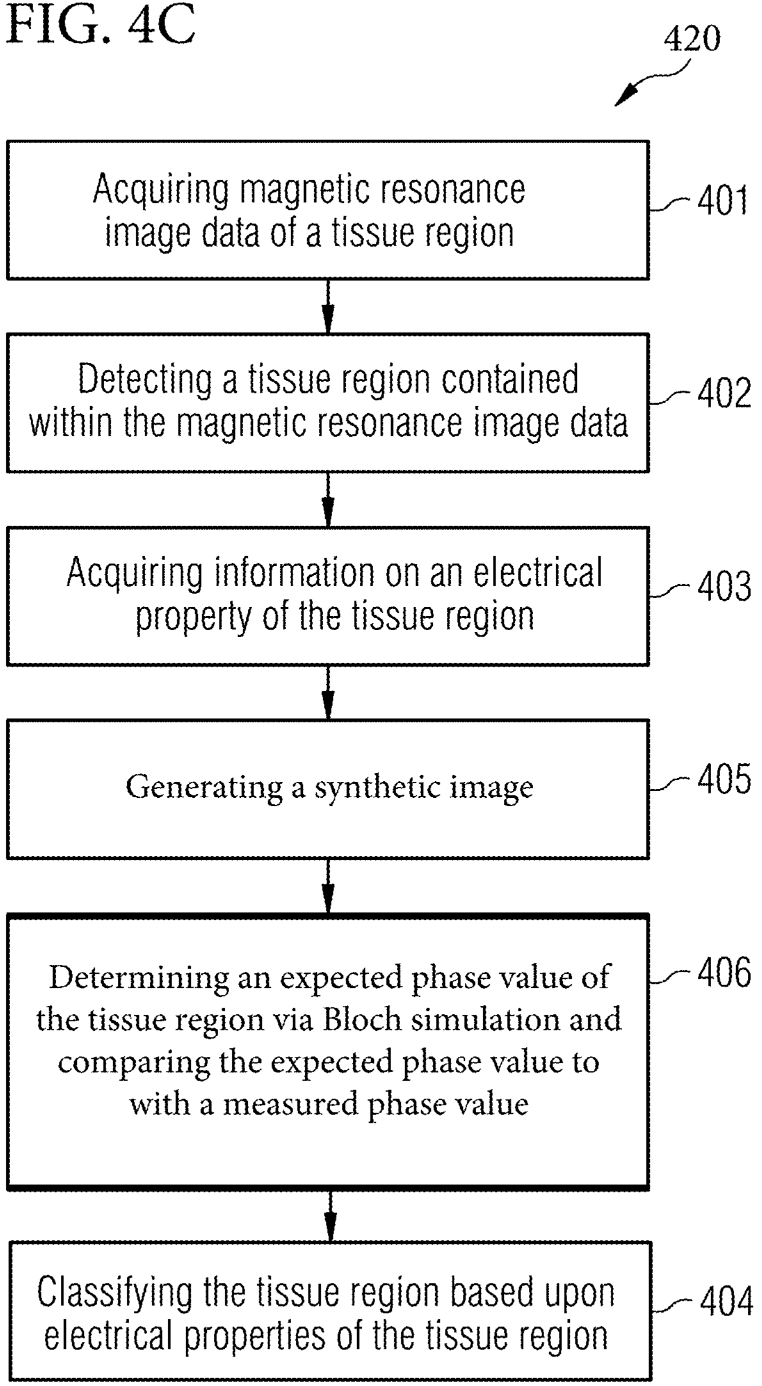
FIG. 4C
420
Acquiring magnetic resonance image data of a tissue region
401
Detecting a tissue region contained within the magnetic resonance image data
402
Acquiring information on an electrical property of the tissue region
403
Generating a synthetic image
405
Determining an expected phase value of the tissue region via Bloch simulation and comparing the expected phase value to with a measured phase value
406
Classifying the tissue region based upon electrical properties of the tissue region
404

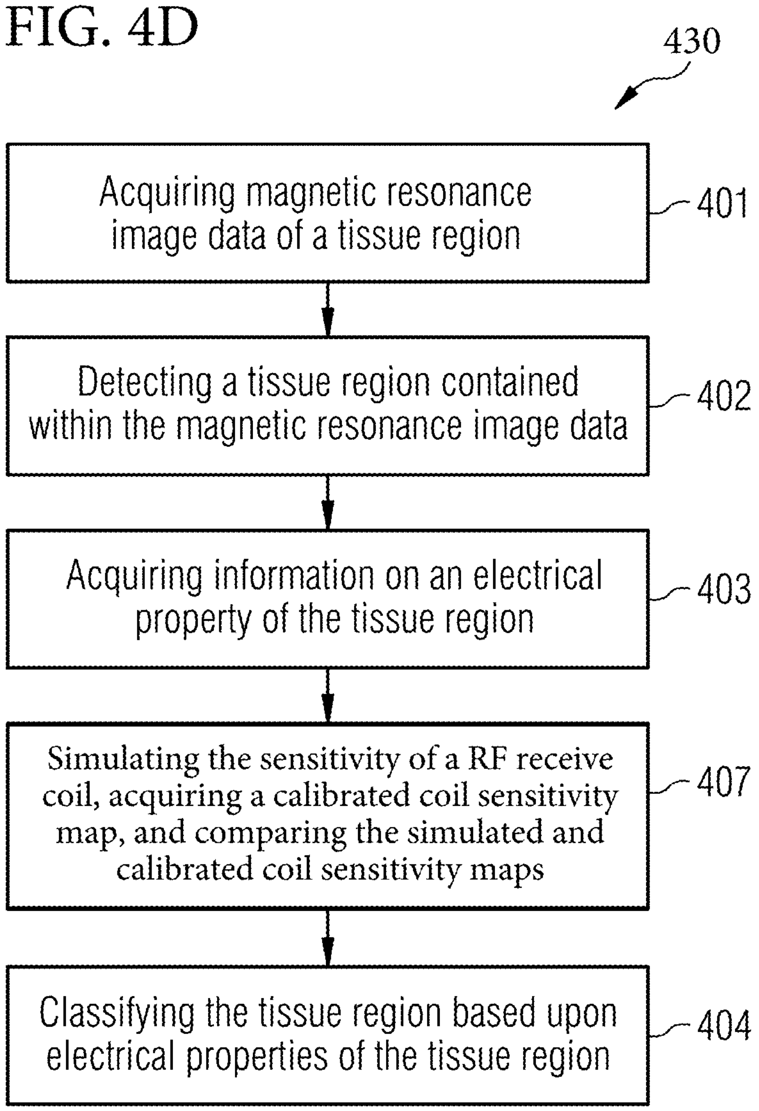
FIG. 4D
430
Acquiring magnetic resonance image data of a tissue region
401
Detecting a tissue region contained within the magnetic resonance image data
402
Acquiring information on an electrical property of the tissue region
403
Simulating the sensitivity of a RF receive coil, acquiring a calibrated coil sensitivity map, and comparing the simulated and calibrated coil sensitivity maps
407
Classifying the tissue region based upon electrical properties of the tissue region
404

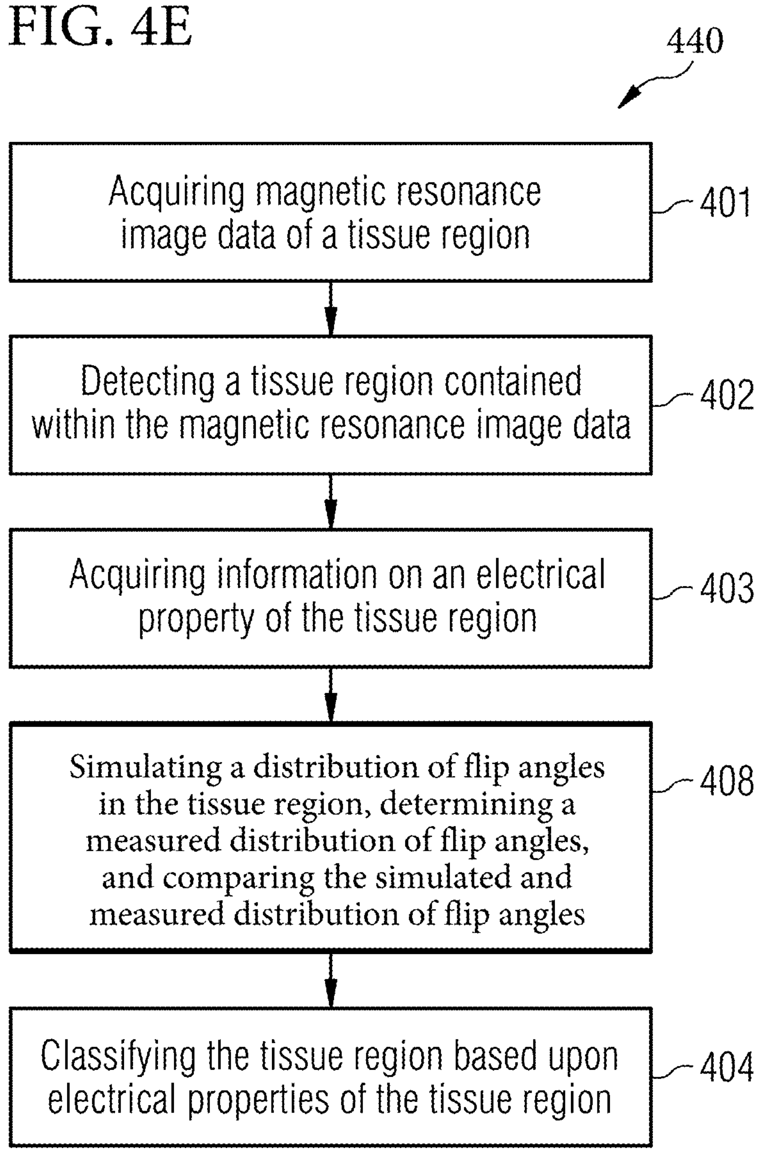
FIG. 4E
440
Acquiring magnetic resonance image data of a tissue region
401
Detecting a tissue region contained within the magnetic resonance image data
402
Acquiring information on an electrical property of the tissue region
403
Simulating a distribution of flip angles in the tissue region, determining a measured distribution of flip angles, and comparing the simulated and measured distribution of flip angles
408
Classifying the tissue region based upon electrical properties of the tissue region
404

TECHNIQUES IMPLEMENTING MRI FOR CANCER CLASSIFICATION

CROSS-REFERENCE TO RELATED APPLICATIONS

The present application claims priority to and the benefit of U.S. provisional patent application no. 63/388,351, filed on Jul. 12, 2022, the contents of which are incorporated herein by reference in their entirety.

TECHNICAL FIELD

The disclosure is directed to improving the specificity of magnetic resonance (MR) cancer screening techniques.

BACKGROUND

Using MRI (magnetic resonance imaging) scanners for screening and diagnostic purposes is a topic of high interest for the healthcare providers. For example, dedicated MRI scanners have been proposed for the detection of prostate cancer PCa or breast cancers BCa. Prostate cancer is considered to be the most common cancer among males. Breast cancer is the most commonly occurring cancer among women and the most common cancer overall. Early and precise diagnosis of cancers is essential for adequate treatment.

The MRI screening for detection of cancers has been proved to be very sensitive, yet it also suffers from weak specificity. Moreover, MRI-based diagnostics may generate many false positive findings that lead to the need for additional tests. The diagnosis of suspicious cancers is confirmed by taking a biopsy of the concerning tissue. Once the first diagnosis is made, further tests are done to determine if the cancer has spread beyond the target organ, and which treatment is most likely to be effective. All these steps are unnecessary for a patient with a false positive finding, and they expose the patient to stress and dissatisfaction and generate high costs for the healthcare system. Thus, the balance of benefits versus the harms of prostate or breast cancer MRI screening is controversial, and there is a need to improve the specificity of MRI detection of clinically-significant cancers for screening purposes.

SUMMARY

A conventional MRI screening method for the detection of clinically significant PCa (csPCa) uses a shorter bi-parametric MRI protocol, which includes T2 and ADC (apparent diffusion coefficient) contrasts. Many small-scale studies and reports regarding such shorter bi-parametric MRI protocols are available, yet the results of these studies have not been validated based on a large sample size. There is a dispute in this context about the role and significance of the dynamic contrast enhanced (DCE) MRI contrast. Some experts argue to include DCE for improving the reliance on MRI findings. However, DCE would increase the costs requiring a venous injection of a contrast agent into the patient's bloodstream. This could be done in a hospital facility, but it would not be easily possible for a point-of-care or a "drugstore scanner" installation.

For breast cancer screening, an abbreviated version of the standard breast MRI protocol consisting of a single early phase dynamic contrast enhanced (DCE) series may be used. Several clinical studies have shown that this MRI protocol does not affect the sensitivity or specificity for breast MRI screening purposes. The diffusion weighted MR imaging (DWI) has also been suggested for improving the BCa diagnostic.

Even though the shorter bi-parameter PCa and the abbreviated breast MRI screening protocol significantly reduce the examination time per patient, and are well-positioned to reduce the overall screening costs, the weakness in low specificity of these MRI methods remains. Thus, there is a need in the art of MRI cancer screening for new methods to improve the specificity while maintaining the high sensitivity of the MRI findings.

Magnetic resonance electrical properties tomography (MR-EPT) is a conventional method aiming to map the spatial distribution of the electrical conductivity and permittivity of body tissues by using measured RF fields (the B1 radiofrequency fields) in a MR scanner.

The electrical properties (EP) of tissues (e. g. the conductivity $\sigma$ and the permittivity c of the tissue) can be assessed via conductivity measurements, and have the potential to be used as biomarkers in many clinical applications. The electrical properties of tissues may depend on a structure and a composition of the tissue. For example, the conductivity of the tissue may vary in dependence of fluid content and/or ionic concentrations, whereas the permittivity of the tissue is largely influenced by an extent and/or configuration of cellular membranes. Cancer typically causes local changes of EPs relative to healthy tissues, which is indicative of tumor progress as expressed by the aggressive tumor angiogenesis. The EPs of benign tissue have been reported to differ from the EPs of tumorous tissue. Conductivity measurements can therefore be used for a better characterization of brain tumors, pelvic tumors (e. g. PCa), breast cancer, and the like.

Conventional MR-EPT methods (e.g. as mentioned in U.S. Pat. Nos. 7,839,147, 9,645,214, or U.S. Pat. No. 9,903,921 which are incorporated herein by reference) usually rely on an application of special sequences of RF (radiofrequency) pulses, a multitude of transmit and receive RF coils, and simplifying assumptions facilitating a separation of a transmit phase from a receive phase of the RF system. These conventional methods are not clinically accessible owing to a strong noise sensitivity, challenges associated with separating the transmit phase and the receive phase, as well as unreliable and unreproducible MRI contrasts. Thus, there is a need for new MR-EPT methods which improve the specificity of cancer screening and avoid the disadvantages of the conventional techniques mentioned above.

BRIEF DESCRIPTION OF THE DRAWINGS/FIGURES

Advantages and details of the present disclosure may be recognized from the examples and embodiments described below as well as the drawings. The figures show:

FIG. 4C illustrates an example flow for classifying a tissue region based upon a comparison of an expected phase value with a measured phase value included in a k-space sample of the magnetic resonance image data of the tissue region;

FIG. 4D illustrates an example flow for classifying a tissue region based upon a comparison of a simulated coil sensitivity map with a calibrated coil sensitivity map; and FIG. 4E illustrates an example flow for classifying a tissue region based upon a comparison of a simulated distribution of flip angles with a measured distribution of flip angles.

DETAILED DESCRIPTION

Figure 1A:
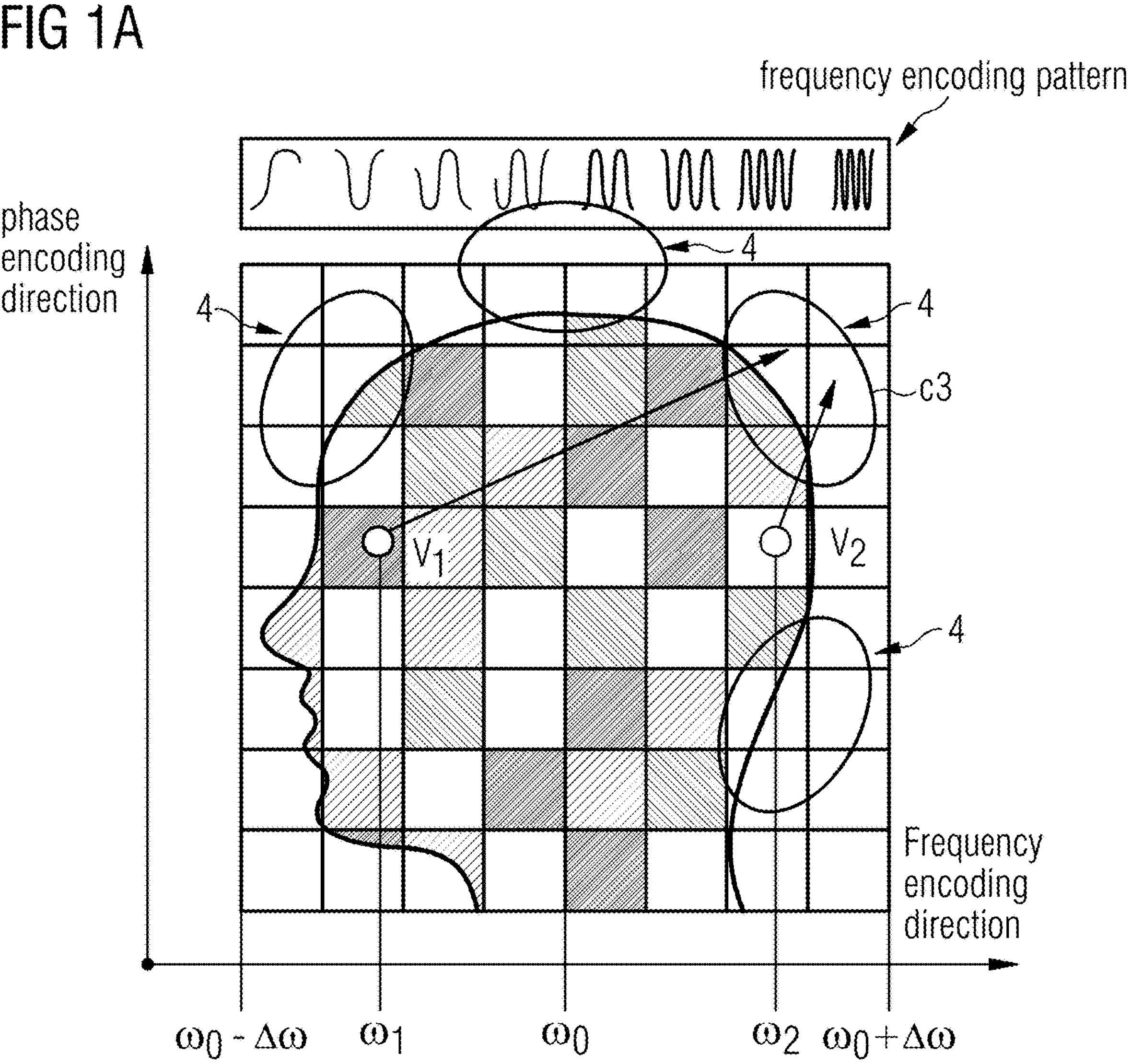
FIG. 1A illustrates an example propagation of receive MR signals toward the receive coils for Cartesian trajectories, in accordance with one or more embodiments of the present disclosure.

I. Introduction of Medical Science Relevant for the Embodiments

Rapidly growing tumors are usually heavily vascularized, while dormant ones are not. Small dormant tumors that are devoid of active blood vessel formation can frequently be observed in human tissues. However, the tumor progression is typically accompanied by an ingrowth of blood vessels, consistent with a need for malignant cells to have access to the bloodstream system to thrive. Consequently, the tumor progression requires an initiation of tumor angiogenesis. A so-called "angiogenic switch" releases tumors from dormancy and sparks rapid growth of malignant cells in association with the formation of new blood vessels. Aggressively growing tumors form vessel-like structures through a process denoted as vascular mimicry. This biological process in turn causes local changes in the electric properties of tumor tissue relative to healthy tissues, which are indicative of tumor progress.

It is a target of this disclosure to use the learnings above to improve the specificity of conventional MR cancer screening methods. To this end, it is noted that a main goal of cancer screening is to detect clinically-significant cancers following standard classification codes. For example, for PCa there is the PI-RADS (Prostate Imaging Reporting and Data System) cancer coding system, taking values on a 1 to 5 scale, and being independent from the imaging modality. A PI-RADS score of 3 or more applies for a suspicious or clinically significant PCa. For BCa there is the BI-RADS (Breast Imaging Reporting and Data System) coding system, taking values on a 0 to 6 scale. BI-RADS scores of 4 or more apply for a clinically significant BCa.

Thus, according to an example, a new MR cancer screening method may deliver a binary output for benign or dormant tumors (i.e. PI-RADS<3, BI-RADS<4), and/or suspicious or malignant tumors (i.e. PI-RADS=3 or more, BI-RADS=4 or more).

The new cancer screening techniques as further described herein in accordance with the various embodiments may be based on or accomplished by detecting local changes in electric properties of tumor tissue relative to healthy tissues. By making use of this data, the specificity of the MRI findings may be improved. A more detailed description of the various embodiments is provided below.

II. Physics Relevant for the Embodiments—the Phase Information in the Raw MR Signals, in the k-Space Data, and in Image Data In typical MRI scanners, analog MR signals received from RF coils may be decoded using a so-called quadrature or I-Q demodulator circuit. Both in-phase (I) and quadrature-phase (Q) outputs of the demodulator circuit may be converted into digital values or samples using a dedicated analog-to-digital converter (ADC) channel for each component. Thus, the digital samples of the received MR signals are stored as complex values, having both an amplitude and a phase. The phase is usually measured or acquired in dependence of a phase of a master clock signal of the MR scanner. Usually, this is known as the transceiver phase, as it accumulates both the transmit phase and the receive phase.

A dephasing of the received MR signals (which are dependent on the phase of the RF pulse applied for stimulating these signals from inside the body) occurs also due to the influence of the electric properties of tissues (e.g. the conductivity $\sigma$ and the permittivity $\varepsilon$) on the accrued phase of the RF signals as they propagate through various tissues. A transmit dephasing may occur, affecting the RF pulses as they travel from a transmit antenna (e.g. a body coil) of the MR scanner into individual voxels of the volume to be imaged. Likewise, a receive dephasing may occur, affecting induced MR signals as they propagate from voxels of the volume to be imaged (e.g. a diagnostically-relevant tissue region) towards the receive RF coils of the MR scanner. The phase information is included in all received MR signals of a MR measuring sequence, and even after signal processing, the phase information propagates into the k-space data as well as into the reconstructed MR images. Usually, the phase information in the reconstructed MR image is not used. Only the magnitude of the pixels (e.g. the gray level) is typically displayed and used for diagnostic purposes or further post-processing steps.

Figure 1B:
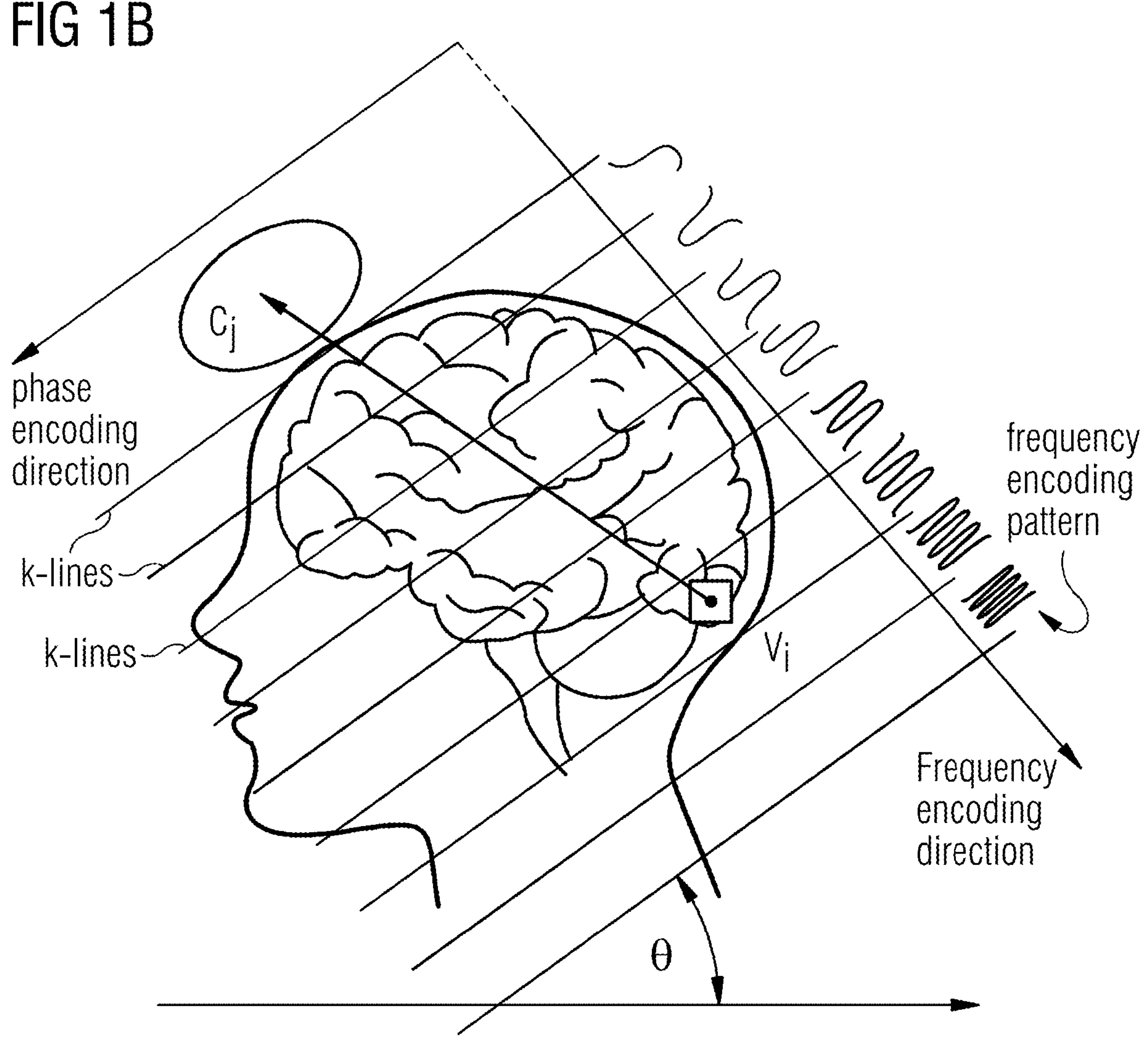
FIG. 1B illustrates an example propagation of receive MR signals toward the receive coils for radial trajectories, in accordance with one or more embodiments of the present disclosure.
Figure 3:
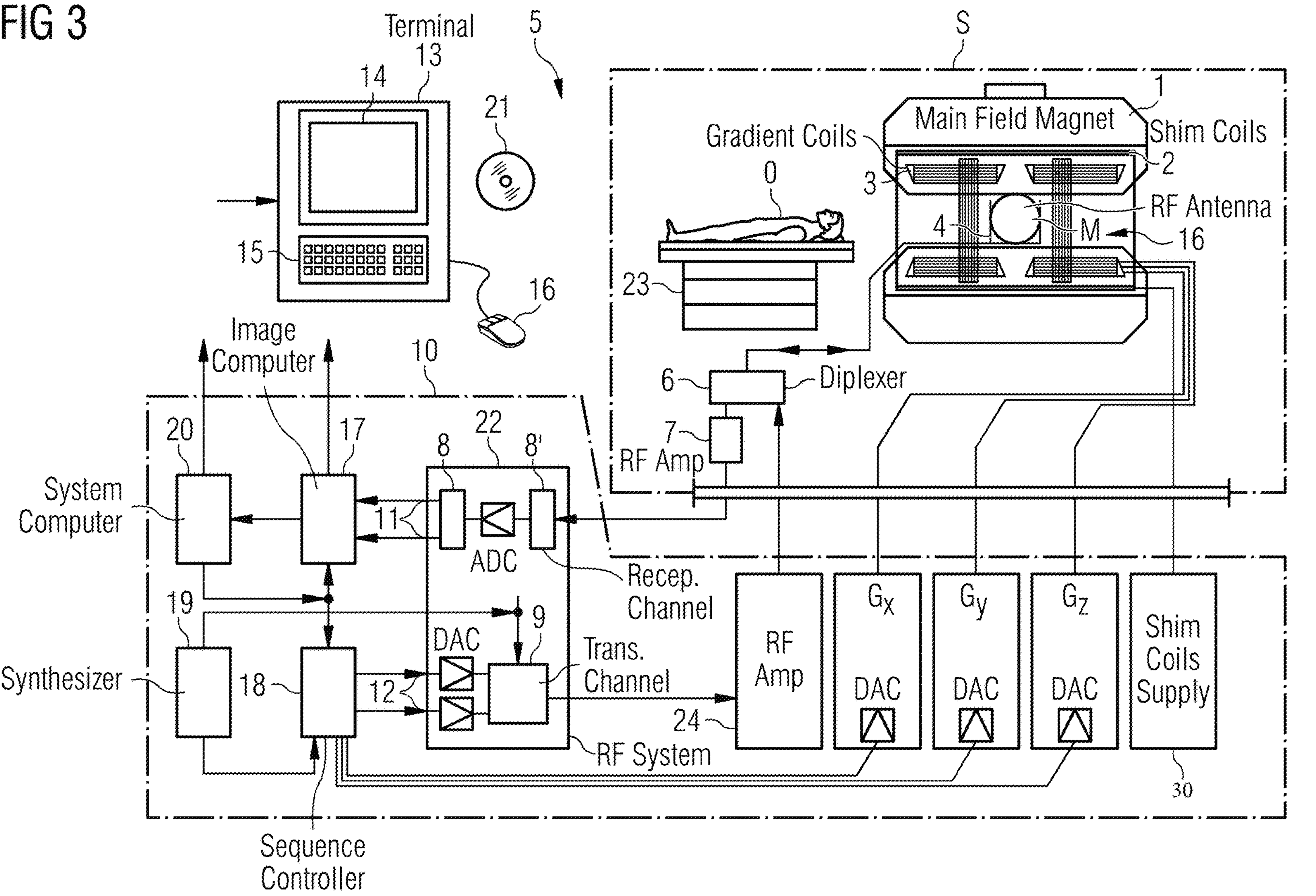
FIG. 3 illustrates a representation of an example magnetic resonance device in accordance with one or more embodiments of the present disclosure.

FIGS. 1A and 1B illustrate the propagation of MR signals towards the receive coils 4 (or radio-frequency antennas) of a magnetic resonance apparatus 5 (see FIG. 3). The phase encoding direction and the frequency encoding direction are also shown, as well as the frequency encoding pattern used for readout. With reference to FIGS. 1A and 1B, the MR voxel signals may originate in various spatial positions (or volumes) $V_1$, $V_2$, etc., and have different frequencies that are dependent upon the frequency encoding pattern used for readout. The amplitude of the received MR signals further depends on the phase encoding pattern being used.

As a result, this phase information, which directly or indirectly reveals the electromagnetic properties of the tissues, can be used to improve the specificity of the MRI findings. A more detailed description of the embodiments is provided below.

In the example shown in FIG. 1A, a signal from a first volume $V_1$ travels through the tissue and is recorded via the receive coil $c_3$. The electrical properties of the tissue modify the signal while it travels through the tissue. A signal from a second volume $V_2$ is also received by the receive coil $c_3$. The phases and amplitudes of the signals from the volume $V_2$ and the volume $V_1$ differ due to the different phase encoding patterns used for encoding the signals from the first volume $V_1$ and the second volume $V_2$. As the second volume $V_2$ is closer to the receive coil $c_3$, lesser modifications of the signal (e.g. due to dephasing of the signal) is to be expected.

In FIG. 1B, radial or spiral trajectories are used to excite nuclear spins within a diagnostically-relevant region of a patient, e.g. the brain of an examination subject such as a patient or object O as shown in FIG. 3. The frequency encoding pattern is constant along the k-lines. However, when using radial or spiral trajectories, the k-lines may be rotated through the angle θ. Thus, a modification of the signal may occur along each k-line as the k-lines are rotated and cross different tissues between a volume element $V_1$ generating the signal and a receive coil $c_j$.

In the examples depicted in FIGS. 1A and 1B, the brain of the patient constitutes the diagnostically-relevant region. However, this is by way of example and ease of explanation, and is not intended to be limiting. Any of the concepts as described herein with respect to FIGS. 1A and 1B may be extended to any other suitable tissue regions, such as, for example, a patient's prostate, breast, etc.

III. Detection and Localization of Suspicious Tissue Regions

Figure 2:
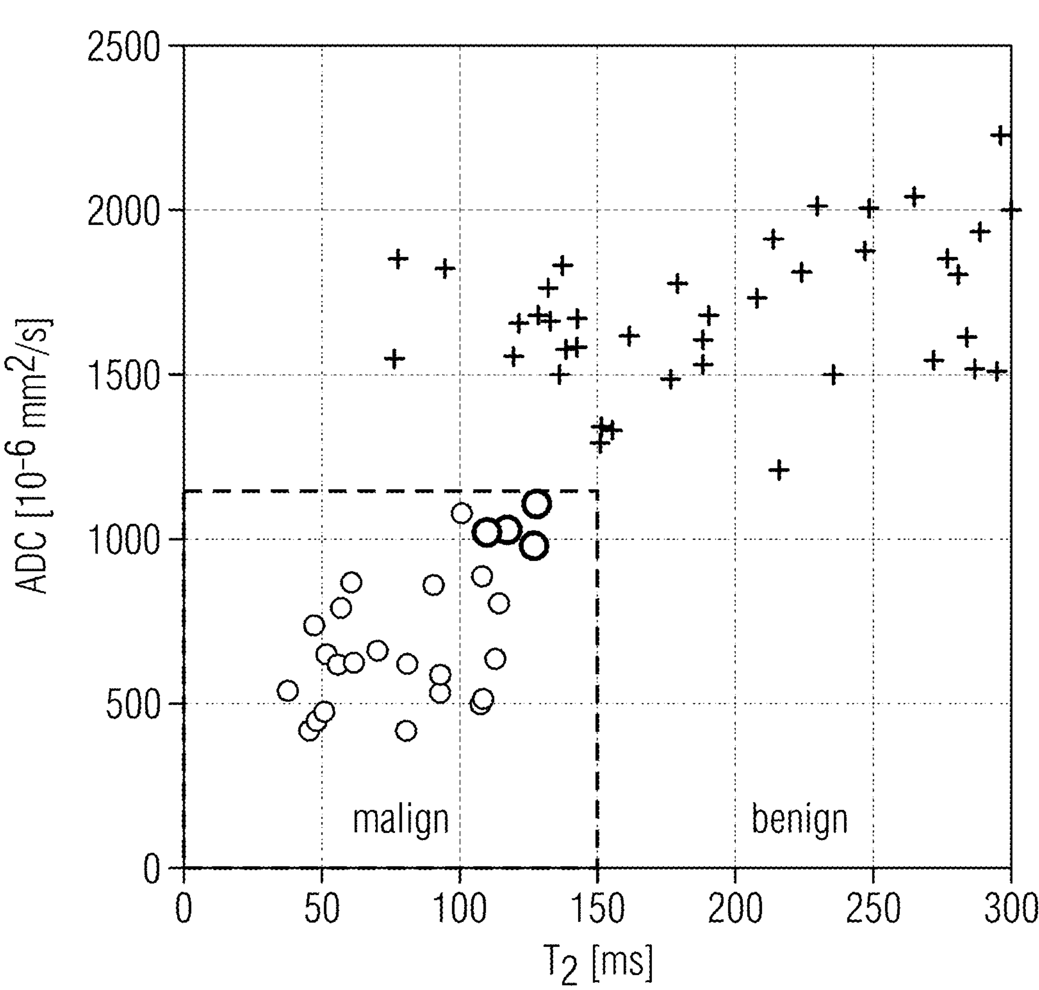
FIG. 2 illustrates an example of typical T2 and ADC values for tissue voxels of various prostate pathologies, in accordance with one or more embodiments of the present disclosure.

An embodiment for the detection of prostate cancer is described below. Again, the detection of prostate cancer is provided for ease of explanation and by way of example and not limitation. Thus, this technique may also be applied to the detection of any other suitable types of cancers or diseases by adapting the MR scan protocols, i.e. the imaging parameters, based on a different target organ and/or disease. In the case of PCa, a screening bi-parametric MRI protocol may provide two images, one for the T2 contrast and a second one for the diffusion or ADC (apparent diffusion coefficient) contrast. FIG. 2 shows typical T2 and ADC values for tissue voxels of various prostate pathologies.

According to an embodiment, image processing may be implemented to detect the tissue region within the images. For instance, anatomical structures in the T2 and ADC images may be segmented and aligned as part of an initial step, for example with a special focus on the prostate region in this example. In a further step, the maximum T2 value (T2_MAX) and ADC value (ADC_MAX) over the prostate region are then determined. Furthermore, the pixel values in both images are normalized by dividing T2 pixel values in the T2 image by the maximum value T2_MAX, and dividing the ADC values in the ADC image by the maximum value ADC_MAX. This may be performed using any suitable techniques, which may include in accordance with Equation 1 below as follows:

$$T2\_N = T2/T2\_MAX \text{ and } ADC\_N = ADC/ADC\_MAX \qquad \text{Eqn. 1:}$$

In accordance with an embodiment, in a further step the normalized pixel values in the two aligned images are then added into a new synthetic image contrast T2_N+ADC_N to generate a synthetic image. The tissue voxels having synthetic values in the normalized range below the T2 and ADC thresholds, as shown in FIG. 2 (e g. T2<150 and ADC<1200), may fall into the category of suspicious tissue (low-grade or high-grade cancer). However, tissue voxels having synthetic values corresponding to a boundary between the benign and malign domains may lead to false positive findings. This issue may be addressed according to an embodiment described below.

IV. Classification of Suspicious Tissue Using the Phase Information to Validate the Clinical Findings According to an embodiment, use is made of the phase information to eliminate or at least reduce false positive findings. As explained above, malign tissue causes changes of the electrical properties (EPs) in comparison to normal or benign tissue, which in turn impacts the phase of the measured MR signals. In contrast to conventional use of MR-EPT, which reconstructs full anatomical images displaying the EP distribution maps over the imaging volume (e.g. the spatial distribution of σ and ε in the tissue region), the embodiments described herein include the use of a new method of indirect MR-EPT. Indirect MR-EPT implicitly detects changes in the EPs of tissues by analyzing the concomitant effects of these changes on parameters that are easier to assess and/or are already available. Using this new method, the specificity of the clinical prediction or the accuracy of a binary-only classification benign/malign tumor may be improved. In the following, exemplary embodiments are described in more detail.

V. Analyzing the Phase Information in k-Space Samples to Detect Changes in the EP of Tumor Tissues In one embodiment, expected phase values for a predetermined number of one or more relevant k-space samples may be determined by using accelerated Bloch simulations. Accelerated Bloch simulations are generally known, for example as disclosed in US20200167975.

Deviations from the expected phase values due to changes in EP parameters within the suspicious tissues may then be determined. To do so, information on an EP value of a tissue region, e.g. information indicative of a normal or malign EP, may be assigned to the suspicious tissue in the generated segmented synthetic image, as discussed in Section III above. Furthermore, EP values may be assigned to the other segmented tissue regions (e.g. muscle, bone, fat, etc.) as available from any suitable number and/or type of various data sources. For example, a table of tissue dielectric proprieties is openly available from the Foundation for Research on Information Technologies in Society (ITIS).

Using electromagnetic simulations, the phase of the MR signals or the phase information in a generated synthetic image may then be predicted and compared to the measured data. If this comparison results in an agreement (e.g. based upon a predetermined threshold), it can be concluded that the suspicious region is indeed a malignancy. In one example, a Bloch simulation using standard values for electrical properties of the tissue region is performed to determine an expected phase value of the tissue region. For this purpose, standard or reference values for electrical properties may be acquired and assigned to voxels of the tissue region. The expected phase value can be compared with a measured phase value of the tissue region included in a corresponding k-space sample of the magnetic resonance image data acquired from the patient. A classification of the tissue region may then be carried out based upon a difference between any suitable number of the expected phase values and the measured phase values.

The simulation may provide any suitable type of information. For instance, according to an embodiment, only selected k-space points or image pixels may be simulated. The selection of k-space points or image pixels for simulation in this manner may comprise those data points which are mostly subjected to dephasing within the suspicious prostate tissue regions. This determination may be based upon any suitable conditions, such as a predefined shape and/or size, a distance from one or more coils, etc. Additionally or alternatively, this determination may be made by recognizing that data points most affected by changes in tissue impedance are those involved with the MR signals collected along frequency lines crossing the suspicious tissue regions. To provide an illustrative example with reference to FIG. 1A, if V1 is a voxel of suspicious tissues, then the data (the signal) having the MR frequency ω1 is the most relevant and would be selected for simulation in this manner A similar judgement may be applied with respect to the tissue voxel V2.

The data points may be correlated with the k-space via the readout patterns over the imaging volume. Again, this is schematically depicted in FIGS. 1A and 1B, which illustrate how each frequency component (e.g. the k-space samples along the frequency encoding direction) is associated with the spatial location of each of the tissue voxels.

VI. Analyzing the Sensitivity Profiles of the RF Receive Coils to Detect Changes in the EP of Tumor Tissues It is known in the art of MRI that sensitivity profiles of the RF receive coils depend on a body region to be imaged. In other words, the body region may influence the operation of the receive coils placed around it. For this reason, any scan sequence and associated image reconstruction steps requires a pre-scan to calibrate the coil sensitivities. Some image reconstruction methods, like for example GRAPPA (GeneRalized Autocalibrating Partial Parallel Acquisition), are known to be auto-calibrated. Yet, these methods also need to acquire autocalibration data in the k-space.

The EPs (e.g. the σ value and the ε value) of body tissues may change or modulate the coil sensitivities. The reason for this behavior is that the tissue regions having a high conductivity and a high dielectric permittivity tend to attenuate and focus the RF fields around it. Thus, a change in an EP caused by tumorous tissue may affect or change the sensitivity profile of a receive coil, thus allowing for a detection of anomalies based on the distribution of EPs.

According to an embodiment, an information on an EP value of a tissue region, e.g. information indicative of a normal or malign EP, may be assigned to a suspicious tissue region, as described in Section V above. For example, the information indicative of a normal or malign EP may comprise information on a correlation between EP values and an expected modification of a sensitivity profile of a receive coil. The coil sensitivities may be simulated to provide coil sensitivity maps, which may be compared with coil sensitivity maps acquired via the calibration step. A difference or degree of match between the simulated coil sensitivity map and the calibrated coil sensitivity map may be determined. A classification of benign or malign tissue can thus be made based on the degree of match or the determined difference (e.g. using a predetermined threshold), and the information on the EP value assigned to the tissue region.

In an embodiment, a simulation of the sensitivity of a RF receive coil 4 is carried out to provide a simulated coil sensitivity map. Furthermore, a pre-scan is conducted using the magnetic resonance scanner 5 to acquire a calibrated coil sensitivity map. The simulated coil sensitivity map is then compared with the calibrated coil sensitivity map, and the tissue region is classified based upon the information on the electrical property of the tissue region and a difference or degree of match (e.g. within a predetermined threshold value) between the simulated coil sensitivity map and the calibrated coil sensitivity map.

VII. Analyzing the B1+ Field Maps to Detect Changes in the EPs of Tumor Tissues

The EPs of tumor tissues can also modulate a transmission profile of an excitation coil, e.g. by modifying an RF signal travelling from the transmit antenna (body coil) into the individual voxels of the volume to be imaged. As explained above, tissue regions having high conductivity and dielectric permittivity tend to attenuate and focus the RF fields around it. Thus, changes in the EP of tumor tissues may change the transmit profiles of the excitation coil, which in turn can be used to detect anomalies in the distribution of EP.

It is known to acquire B1+ maps showing the inhomogeneity of flip angles over the imaging volume. Regions of high electrical conductivity and dielectric permittivity tend to generate larger inhomogeneities of the flip angle. An inhomogeneity of the flip angle or an inhomogeneity of the B1+ field directly translates into local inhomogeneities of brightness in a reconstructed MR image. Thus, stronger inhomogeneities can be expected when malign tumors are present within the imaging area.

The embodiments described herein may comprise the acts of simulating a distribution of flip angles and assigning information on an EP value to the suspicious tissues, as described in Section V above. For example, standard values for the electrical properties of the tissue region may be used for simulating the distribution of flip angles (e.g. standard values for the electrical properties of the tissue may be assigned to the respective tissue regions). The information indicative of a normal or malign EP may also comprise information on a correlation between EP values and an expected distribution of flip angles in the tissue region. The results of the simulation may be compared with a measured distribution of flip angles, and a classification of benign or malign tissue may be carried out based on this comparison (e.g. a difference or degree of match within a predetermined threshold value).

According to an embodiment, a distribution of flip angles in the tissue region is simulated. Furthermore, magnetic resonance image data from the tissue region is acquired using the magnetic resonance system 5, and a measured distribution of flip angles is determined based on the magnetic resonance image data. The simulated distribution of flip angles is then compared with the measured distribution of flip angles, and the tissue region is classified based upon the information on the electrical property of the tissue region and a difference or degree of match (e.g. within a predetermined threshold value) between the simulated distribution of flip angles and the measured distribution of flip angles.

VIII. Using Machine Learning (ML) and Artificial Intelligence (AI) Methods to Classify Tumors Alternatively or in addition to the embodiments described above (e.g. the embodiments described in any of Sections V, VI, and/or VII) ML and/or AI methods may be implemented to avoid time intensive simulation steps and/or to accelerate the classification task in a screening settings at e.g. point-of-care or drugstore facilities.

For example, to accelerate the method as described in Section V, an end-to-end AI classifier may be trained with real clinical data (e.g. MR signals or MR images) to learn and recognize the characteristic patterns in the phase of MR data that distinguishes a malignancy. For acceleration of the method as described in Section VI, an AI classifier may be trained with a suitable amount of clinical data, and thus directly detect the characteristic anomalies in the coil sensitivities. To accelerate the method as described in Section VII, an AI classifier may be trained with a suitable amount of clinical data, which may then directly detect the characteristic anomalies in the distribution of flip angle or B1+ field.

In each case, information on an electrical property of the tissue region may be provided or included in the training data or clinical data used to train each respective AI classifier. It is noted that any suitable AI and/or ML system may be implemented for this purpose, which may include a neural network having any suitable number of input, hidden, and output layers to facilitate this classification process.

IX. An Example Magnetic Resonance Device

FIG. 3 illustrates a representation of an example magnetic resonance device in accordance with one or more embodiments of the present disclosure. The components within the dot-dash outline S are commonly referred to as a magnetic resonance scanner, a magnetic resonance data acquisition scanner, or simply a scanner. The components within the dot-dash outline 10 are commonly referred to as a control unit, a control device, a controller, or a control computer.

As shown in FIG. 3, a magnetic resonance apparatus 5 (e.g. a magnetic resonance imaging device, a magnetic resonance tomography device, or a magnetic resonance scanner) is shown. The magnetic resonance apparatus 5 may be configured to perform MRI imaging scans or measurements in accordance with any suitable sequence and/or techniques, e.g., 2D slice-by-slice or 3D volume acquisitions that may incorporate encoding techniques, such as Simultaneous Multi-Slice (SMS) or Controlled Aliasing in Parallel Imaging Results in Higher Acceleration (CAIPRINHA). The magnetic resonance apparatus 5 may include additional, fewer, or alternate components that are not depicted in FIG. 3 for purposes of brevity. For instance, the magnetic resonance apparatus 5 may alternatively include, or include in addition to the depicted DVD 21, one or more non-transitory computer-readable data storage media in accordance with various embodiments of the present disclosure. Thus, the aforementioned non-transitory computer-readable media may be loaded, stored, accessed, retrieved, etc., via one or more components accessible to, integrated with, and/or in communication with the magnetic resonance apparatus 5 (e.g., network storage, external memory, etc.). For example, such data-storage mediums and associated program code may be integrated and/or accessed via the terminal 13, the control device 10, or components thereof such as the control computer 20, the image computer 17, the sequence controller 18, the RF system 22, etc.

A main field magnet system 1 is configured to generate a temporally-constant and strong magnetic field (main magnetic field or B0 field) for the polarization or alignment of the nuclear spins in a tissue region of an examination subject (e.g. a patient) or object O, such as a portion of a human body that is to be examined, and who is lying on a table 23 to be moved into the magnetic resonance apparatus 5. The high degree of homogeneity in the magnetic field generated via the main field magnet system 1 necessary for the magnetic resonance measurement (data acquisition) is defined in a typically sphere-shaped measurement volume M, in which the portion of the human body that is to be examined is placed. To support the homogeneity requirements, temporally-constant effects are eliminated by shim-plates made of ferromagnetic materials that are placed at appropriate positions. Temporally-variable effects are eliminated by shim-coils 2 and an appropriate control unit for the shim-coils 2 (not shown).

A cylindrically-shaped gradient coil system 3 (or alternatively, gradient field system) comprising three windings is incorporated in the main field magnet system 1. The gradient field system 3 is also used to apply a magnetic field gradient, which determines the magnetic resonance frequency (Larmor frequency) at the respective location. Each winding is connected to a corresponding amplifier Gx, Gy, and Gz, with power for generating a linear gradient field in a respective axis of a Cartesian coordinate system. A first winding of the gradient field system 3 generates a gradient Gx in the x-axis, a second winding generates a gradient Gy in the y-axis, and a third winding generates a gradient Gz in the z-axis. Each corresponding amplifier Gx, Gy, and Gz has a digital-analog converter (DAC), controlled by a sequence controller 18 for the accurately-timed generation of gradient pulses. The gradient field system 3 may utilize one or more of the first, second, or third windings of the gradient field system 3 to generate one or more gradients in one or more of the x-axis, the y-axis, and/or the z-axis using a respective Gx, Gy, and/or Gz amplifier. The generated gradients may be used in conjunction with a transmitted RF pulse to receive and process data during acquisition time periods referred to as echoes.

A radio-frequency (RF) antenna 4 is located within an imaging region 16 circumferentially enclosed by the main field magnet. The radio-frequency (RF) antenna 4 is used to convert the RF pulses provided by a radio-frequency power amplifier 24 into a magnetic alternating field for the excitation of nuclei by tipping (i.e. "flipping") the spins in the subject or the region thereof to be examined from the alignment produced by the magnetic field generated via the main field magnet system 1. The radio-frequency antenna 4 may comprise one or more RF receiving coils, as well as one or more RF transmitting coils, in the form of an annular, linear, or matrix type configuration of coils. As the excited nuclear spins relax, RF signals, referred to as magnetic resonance (MR) signals, are emitted in a resonant manner, being received by the RF antenna 4, and then further processed.

Thus, the alternating field provided by precessing nuclear spins, i.e., the nuclear spin echo signal normally produced from a RF pulse sequence comprising one or more RF pulses and one or more gradient pulses, can be converted by the RF receiving coils of the radio-frequency antenna 4 into a voltage (measurement signal), which is transmitted to a radio-frequency system 22 via an RF amplifier 7 of a radio-frequency receiver channel 8, 8'.

The acquisition of the MR signals takes place in the spatial frequency space or "k-space," with k-space being temporally traversed along a "gradient trajectory" that is defined by the switching of the gradient pulses during measurement while the RF pulses are transmitted in a time-coordinated manner. In other words, the MR signals are recorded as "raw data" in k-space along a particular k-space trajectory that is dependent upon the timing of the particular transmitted gradient pulse sequence. The desired image data can then be reconstructed from the recorded raw data in k-space thus acquired by means of a two-dimensional Fourier transform.

The radio-frequency system 22 further includes a transmitting channel 9, in which the RF pulses for the excitation of the magnetic nuclear resonance are generated. For this purpose, the respective RF pulses are digitally represented in the sequence controller 18 as a series of complex numbers, based on a given pulse sequence provided by the system computer 20. This number series is sent via an input 12, in each case, as real and imaginary number components to a digital-to-analog converter (DAC) in the radio-frequency system 22 and from there to the transmitting channel 9. The pulse sequences are modulated in the transmitting channel 9 to a RF carrier signal, the base frequency of which corresponds to the resonance frequency of the nuclear spin in the measurement volume. The modulated pulse sequences of the RF transmitter coil are transmitted to the RF antenna 4 via an amplifier 24. Although a single transmission channel and receiving channel are shown and described with reference to FIG. 3, this is for purposes of brevity and provided by way of example and not limitation. The embodiments herein include acquiring MR signals using any suitable type of imaging technique. Thus, the magnetic resonance apparatus 5 may include any suitable number of receiving and/or transmission channels configured for this purpose, and the radio-frequency system 22 may be further modified to facilitate the control, transmission, and reception of data in accordance with any suitable number of such channels.

Switching from a transmitting to a receiving operation occurs via a transmission-receiving switch 6. The RF transmitting coil of the radio-frequency antenna 4 radiates the radio-frequency pulse for the excitation of the nuclear spins in the measurement volume M, and scans the resulting echo signals via the RF receiving coils. The corresponding magnetic resonance signals obtained thereby are demodulated to an intermediate frequency in a phase-sensitive manner in a first demodulator 8' of the receiving channel of the radio-frequency system 22, and digitized in an analog-digital converter (ADC). This signal is then demodulated to the base frequency. The demodulation to the base frequency and the separation into real and imaginary parts occurs after digitization in the spatial domain in a second demodulator 8, which emits the demodulated data via outputs 11 to an image processor 17.

Therefore, generally predefined pulse sequences determined during measurement, in other words sequences of defined RF pulses, as well as gradient pulses in different directions and read-out windows, are used to activate a magnetic resonance tomography system while the receive antennas are switched to receive, and the MR signals are acquired via the process of receiving, processing, and recording these signals as raw data in k-space. The predefined pulse sequences are generally established beforehand in accordance with any suitable type of measurement protocol together with other control data for the measurement.

In an image processor or image computer 17, an MR image is reconstructed from the obtained measurement data (e. g. the raw data recorded in k-space, which may be referred to herein as acquired k-space data). The reconstruction of the MR image from the measurement data may comprise a computation of at least one disturbance matrix and an inversion thereof, in the image processor 17. The measurement data, the image data, and the control program is handled or managed via the system computer 20. The sequence controller 18 controls the generation of the desired pulse sequences and the corresponding scanning of k-space with control programs. The sequence controller 18 controls accurately-timed switching (activation) of the gradients, the transmission of the radio-frequency pulse with a defined phase amplitude, and the reception of the magnetic resonance signals. The time base for the radio-frequency system 22 and the sequence controller 18 is provided by a synthesizer 19. The system computer 20 may control the selection of appropriate control programs for the generation of an MR image, which are stored, for example, on a DVD 21 or other suitable storage media. The display of the generated MR images may be facilitated via a terminal 13, which includes units for enabling input entries, such as, e. g. a keyboard and/or a mouse 16, and a unit for enabling a display, such as, e.g. a display screen 14.

Thus, the magnetic resonance apparatus 5 as shown in FIG. 3 may include various components to enable and/or facilitate the measurement, collection, and/or recording of MR signals as raw data or k-space data, as well as reconstructing image data from the measured MR signals. Any of the embodiments described herein may be executed by one or more components of the magnetic resonance apparatus 5, such as for instance the control device 10. For example, the embodiments described herein may be implemented via one or more of the components of the control device 10, such as the system computer 20, the image computer 17, etc. The techniques as discussed herein may be implemented as an algorithm that may be executed via any of the components of the magnetic resonance apparatus 5 or other components that may be in communication with and/or coupled the magnetic resonance apparatus 5, which may or may not be shown in the Figures. For example, the techniques as discussed herein may be enabled via execution of computer-readable instructions by one or more of the components of the control device 10. The computer-readable instructions may be stored in any suitable type of machine-readable medium (e. g. a non-transitory computer-readable medium) integrated with the control device 10 or other suitable location accessible via the control device 10. The components of the control device or other suitable components that may execute such computer-readable instructions, may comprise any suitable number and/or type of processors, processor circuitry, hardware circuitry, etc.

X. Example Flows

Figure 4A:
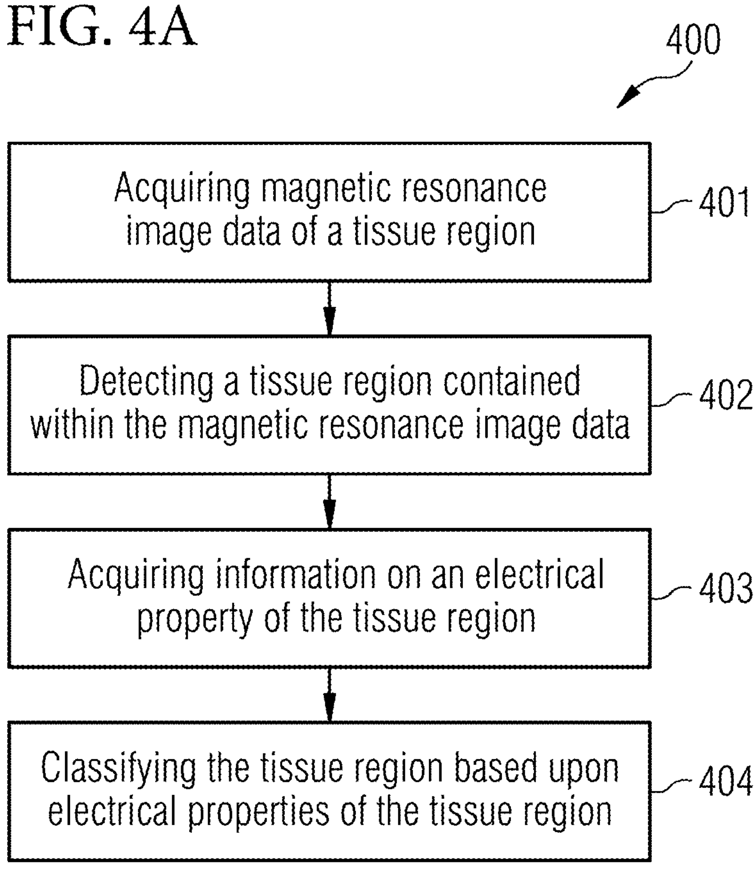
FIG. 4A illustrates an example flow for classifying a tissue region based upon electrical properties, in accordance with one or more embodiments of the present disclosure.

FIGS. 4A-4E illustrate respective example flows for classifying a tissue region based upon electrical properties, in accordance with one or more embodiments of the present disclosure. It is noted that some of the various blocks as shown in FIG. 4A are also common among the various flows as shown in FIGS. 4B-4E, and thus only differences between these blocks and flows will be further described herein with respect to the flows shown in FIGS. 4B-4E.

Any of the example flows as shown in FIGS. 4A-4E may be implemented via software, hardware, or combinations of these. For example, the example flows may be implemented as an algorithm executed by one or more suitable components as discussed above, which may comprise components of the magnetic resonance apparatus 5, such as for instance the control device 10 and/or components thereof. As another example, the example flows as shown in FIGS. 4A-4E may be executed by hardware components identified with one or more components of the magnetic resonance apparatus 5, such as an application specific integrated circuit (ASIC) or other suitable processors, processing circuitry, hardware circuitry, etc., including known configurations and types.

The example flow 400 as shown in FIG. 4A may include acquiring (block 401) magnetic resonance image data of a tissue region. This may include, for instance, acquiring magnetic resonance data of a tissue region of a patient or object O via the magnetic resonance apparatus 5, as discussed herein. The example flow further includes detecting (block 402) a tissue region contained within the magnetic resonance data and determining (block 403) electrical properties of the tissue region as discussed herein. The example flow 400 further includes classifying (block 404) the tissue region based upon electrical properties (EP) thereof, as further discussed herein.

The act of acquiring (block 401) the magnetic resonance image data comprises carrying out a magnetic resonance measurement and/or a pre-scan of a tissue region using a magnetic resonance scanner 5. The acquired magnetic resonance image data may comprise raw data (e.g. magnetic resonance signals received by receive coils 4), as well as k-space data, processed magnetic resonance signals, and/or a reconstructed magnetic resonance image of the tissue region, etc. In one embodiment, a pre-scan is used to acquire the magnetic resonance image data. It is conceivable that a calibrated coil sensitivity map according to an embodiment described herein is derived from the magnetic resonance image data acquired via the pre-scan.

The act of detecting (block 402) the tissue region contained within the magnetic resonance image data may comprise the use of any suitable image processing techniques, including known techniques. This may comprise, for example, segmenting and aligning anatomical structures in a magnetic resonance image or magnetic resonance image data. The anatomical structures may be dependent upon the type of tissue and cancer screening that may be performed. For instance, the anatomical structures may comprise a patient's brain, prostate, breast, etc. In an embodiment, T2 and ADC images are used as a basis for segmenting and aligning the anatomical structures, as noted in accordance with the various embodiments described above.

The act of acquiring (block 403) information on an electrical property (EP) of the tissue region may comprise carrying out any suitable type of MR-EPT measurement of the tissue region. This may include, for example, the MR-EPT measurement techniques as described above. As used herein, the information on the electrical property of the tissue region acquired in this manner may comprise any suitable type of information used for cancer screening purposes as discussed herein. For example, the information on an electrical property of the tissue region may comprise one or more of information indicative of a normal and/or malignant tissue EP value, a standard or reference EP value of a tissue region, an actual and/or measured EP value, "indirectly acquired" EP values as further discussed herein, etc. As another example, in some embodiments, the information on the electrical property of the tissue region may comprise information with respect to concomitant effects of changes of the electrical properties of the tissue region.

As further examples, in some embodiments the information on an electrical property of the tissue region may comprise standard or reference values of the conductivity and/or the dielectric permittivity of the tissue region. These standard values may be assigned to the tissue region, and may serve as a basis for simulations of expected phase values of the tissue region, a sensitivity of the radiofrequency coil 4, and/or a distribution of flip angles in the tissue region according to the embodiments further described herein. The information on an electrical property of the tissue region may also be acquired in connection with clinical data or training data used to train machine learning and/or AI algorithms configured for classifying the tissue region based upon phase information in k-space samples, sensitivity profiles of radiofrequency receive coils, and/or B1+ field maps. In any event, such information on the electrical property of the tissue region may then be used to classify (block 404) the tissue region, as further discussed herein.

Figure 4B:
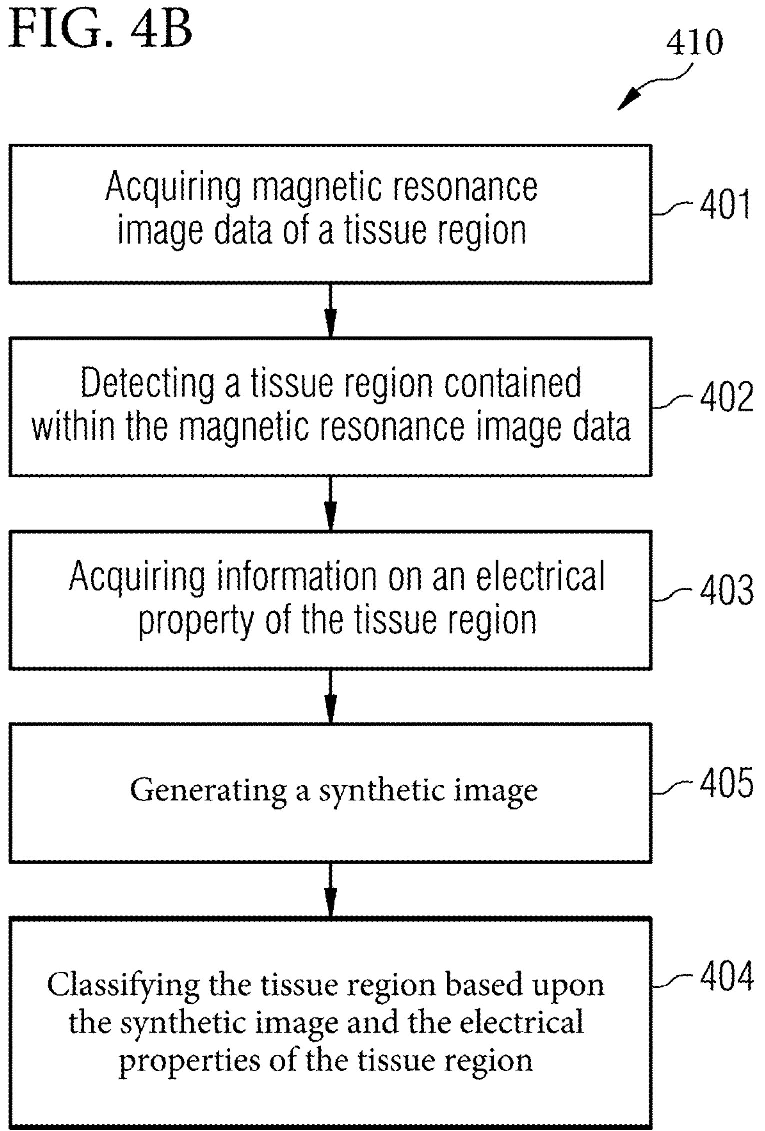
FIG. 4B illustrates an example flow for classifying a tissue region based upon the synthetic image as well as the electrical properties of the tissue region.

The act of acquiring (block 401) the magnetic resonance image data may comprise acquiring a first image and a second image of the tissue region of any suitable types. For example, the first image may comprise a T2-weighted image, and the second image may comprise a diffusion image. In such a case, and turning now to FIG. 4B, according to an embodiment the flow 410 may further comprise the act of determining (block 405) a maximum T2 value and a maximum ADC value of the tissue region, normalizing (block 405) pixel values in the first image and the second image in dependence of the maximum T2 value and the maximum ADC value, and adding (block 405) the normalized pixel values into a synthetic image contrast to generate (block 405) a synthetic image. Again, the act of determining (block 403) electrical properties of the tissue region may comprise acquiring electrical properties of the tissue region via an MR-EPT measurement. Thus, a suspicious region in a synthetic image may be confirmed via the information from the corresponding EP information. Thus, for the flow 410 as shown in FIG. 4B, the act of classifying (block 404) the tissue region may be based upon the synthetic image as well as the electrical properties of the tissue region, thus increasing an accuracy of cancer classification over known methods. Therefore, the classification of the tissue region may be performed as a combination of both a synthetic image and EP mapping that improves the specificity and sensitivity of the PCa diagnostic. It is noted that the EP mapping alone provides cancer detection with lower a specificity.

According to a further embodiment as represented by the flow 420 of FIG. 4C, the flow 420 comprises the further acts of determining (block 406) an expected phase value of a tissue region via a Bloch simulation, and comparing (block 406) the expected phase value with a measured phase value included in a k-space sample of the magnetic resonance image data of the tissue region. Thus, in this example, the Bloch simulation is separate from the generation of the synthetic image. By comparing the expected phase value from the Bloch simulation with a measured phase value, "indirect EP information" is acquired. This indirect EP information may then be used to confirm a suspicious region in the synthetic image.

In this example, the act of acquiring (block 403) information on an electrical property of the tissue region may comprise acquiring (block 403) standard or reference values of the conductivity and/or the dielectric permittivity of the tissue region, and assigning (block 403) these standard values to voxels of the tissue region as a basis for the Bloch simulation. The act of classifying (block 404) the tissue region is thus based, in this scenario, upon a difference between the expected phase values and the measured phase values. That is, the classification may be performed, for instance, based upon whether the corresponding values deviate from one another in excess of a predetermined threshold value of differences, a predetermined percentage deviation, etc.

According to a further embodiment as represented by the flow 430 of FIG. 4D, the flow comprises the further acts of simulating (block 407) the sensitivity of the radiofrequency (RF) receive coil 4 to provide a simulated coil sensitivity map, performing (block 407) a pre-scan to acquire a calibrated coil sensitivity map, and comparing (block 407) the simulated coil sensitivity map with the calibrated coil sensitivity map. In this case, the act of acquiring (block 403) information on an electrical property of the tissue region may comprise acquiring standard or reference values of the conductivity and/or the dielectric permittivity of the tissue region, and assigning these standard values to voxels of the tissue region as a basis for the simulation of the coil sensitivity map. The act of classifying (block 404) the tissue region is thus based, in this scenario, upon a match between the simulated coil sensitivity map and the calibrated coil sensitivity map. For instance, a "match" in this context may include determining whether corresponding values from the simulated coil sensitivity map and the calibrated coil sensitivity map are sufficiently close to one another or deviate from one another. Such a determination may be performed, for instance, based upon whether the corresponding values meet or exceed a predetermined threshold value of differences, a predetermined percentage deviation, etc.

According to a further embodiment as represented by the flow 440 of FIG. 4E, the flow comprises the further acts of simulating (block 408) a distribution of flip angles in the tissue region, determining (block 408) a measured distribution of flip angles based on the magnetic resonance image data, and comparing (block 408) the simulated distribution of flip angles with the measured distribution of flip angles. In this case, the act of acquiring (block 403) information on an electrical property of the tissue region may comprise acquiring standard or reference values of the conductivity and/or the dielectric permittivity of the tissue region, and assigning these standard values to voxels of the tissue region as a basis for the simulation the distribution of flip angles in the tissue region. The act of classifying (block 404) the tissue region is thus based, in this scenario, upon a match between the simulated coil sensitivity map and the calibrated coil sensitivity map. As noted above for the flow 430, the "match" in this context may include determining whether corresponding values from the simulated distribution of flip angles and the measured distribution of flip angles are sufficiently close to one another. Such a determination may be performed, for instance, based upon whether the corresponding distributions meet or exceed a predetermined threshold value of differences, a predetermined percentage deviation, etc.

Although not shown for purposes of brevity, embodiments may also include the flows 430, 440 as shown in FIGS. 4D and 4E further comprising the acts of determining (block 405) a maximum T2 value and a maximum ADC value of the tissue region, normalizing (block 405) pixel values in the first image and the second image in dependence of the maximum T2 value and the maximum ADC value, and adding (block 405) the normalized pixel values into a synthetic image contrast to generate a synthetic image as explained in connection with FIG. 4B. In such scenarios, the act of classifying (block 404) the tissue region may be based upon the synthetic image as well as the electrical properties of the tissue region.

In some embodiments, the classification (block 404) as described in any of the above-referenced flows may be performed based on the information from the matching alone. In other embodiments, the classification (block 404) as described in any of the above-referenced flows may be performed based upon the synthetic image (when applicable) and the information from the matching, which may comprise the aforementioned "indirect EP information." In other words, for each of the embodiments as described herein, the classification of the tissue may be based on the synthetic image and the "indirect EP information," although a synthetic image may not be required in each case. However, it is noted that the combination of a synthetic image and either the direct or indirect EP mapping may be particularly advantageous and may provide the best results.

The embodiments described above are to be recognized as examples. It is to be understood that individual embodiments may be extended by or combined with features of other embodiments if not stated otherwise. Further, the described embodiments are not to be limited to a specific sequence of acts. Individual steps or acts may be carried out in a different order and/or at least partially overlap in time.

The various components described herein may be referred to as "devices" or "units." As noted above, such components may be implemented via any suitable combination of hardware and/or software components as applicable and/or known to achieve the intended respective functionality. This may include mechanical and/or electrical components, processors, processing circuitry, or other suitable hardware components configured to execute instructions or computer programs that are stored on a suitable computer readable medium. Regardless of the particular implementation, such devices and units, as applicable and relevant, may alternatively be referred to herein as "circuitry," "processors," or "processing circuitry."

What is claimed is:

1. A method for classifying a tissue region based on magnetic resonance image data, comprising:

acquiring magnetic resonance image data of a tissue region by acquiring a first image and a second image of the tissue region, the first image being a T2-weighted image and the second image being a diffusion image;

detecting the tissue region contained within the magnetic resonance image data;

determining a maximum T2 value and a maximum apparent diffusion coefficient (ADC) value of the tissue region;

normalizing pixel values within the first image dependent on the maximum T2 value;

normalizing pixel values within the second image dependent on the maximum ADC value;

adding the normalized pixel values into a synthetic image contrast to generate a synthetic image;

acquiring information on an electrical property of the tissue region; and classifying the tissue region based upon the synthetic image and the acquired information on the electrical property of the tissue region.

2. The method according to claim 1, wherein the first image and the second image are acquired via a bi-parametric magnetic resonance imaging protocol.

3. The method according to claim 1, wherein classifying the tissue region comprises:

analyzing phase information in k-space samples of the magnetic resonance image data to detect changes in the electrical property of the tissue region.

4. The method according to claim 3, further comprising:

determining an expected phase value of the tissue region via a Bloch simulation; and comparing the expected phase value with a measured phase value included in a k-space sample from among the k-space samples, wherein the acquired information on the electrical property of the tissue region is assigned to voxels of the tissue region, and wherein the tissue region is classified based upon a difference between the expected phase value and the measured phase value.

5. The method according to claim 1, wherein classifying the tissue region comprises:

using a machine learning and/or artificial intelligence algorithm to classify the tissue region based upon phase information in k-space samples, sensitivity profiles of radiofrequency (RF) receive coils, and/or B1+field maps.

6. The method according to claim 1, wherein detecting the tissue region contained within the magnetic resonance image data comprises:

segmenting and aligning an anatomical structure in the first image and the second image.

7. The method according to claim 1, wherein the magnetic resonance image data comprises a section of a prostate of a patient or a section of a breast of a patient.

8. The method according to claim 1, wherein the tissue region comprises a diagnostically-relevant tissue region that includes a cancerous tissue region or a tumorous tissue region.

9. The method according to claim 1, wherein the electrical property of the tissue region comprises a dielectric permittivity or a conductivity.

10. The method according to claim 1, wherein classifying the tissue region comprises:

outputting information indicative of (i) a benign or dormant tumor, and/or (ii) a suspicious or malignant tumor.

11. A magnetic resonance imaging device, comprising:

first processing circuitry configured to generate magnetic resonance image data associated with a patient; and second processing circuitry configured to:

acquire magnetic resonance image data of a tissue region of the patient by acquiring a first image and a second image of the tissue region, the first image being a T2-weighted image and the second image being a diffusion image;

detect the tissue region contained within the magnetic resonance image data;

determine a maximum T2 value and a maximum apparent diffusion coefficient (ADC) value of the tissue region;

normalize pixel values within the first image dependent on the maximum T2 value;

normalize pixel values within the second image dependent on the maximum ADC value;

add the normalized pixel values into a synthetic image contrast to generate a synthetic image;

acquire information on an electrical property of the tissue region; and classify the tissue region based upon the synthetic image and the acquired information on the electrical property of the tissue region.

12. The magnetic resonance imaging device according to claim 11, wherein the first image and the second image are acquired via a bi-parametric magnetic resonance imaging protocol.

13. The magnetic resonance imaging device according to claim 11, wherein detecting the tissue region contained within the magnetic resonance image data comprises:

segmenting and aligning an anatomical structure in the first image and the second image.

14. The magnetic resonance imaging device according to claim 11, wherein the electrical property of the tissue region comprises a dielectric permittivity or a conductivity.

15. A method for classifying a tissue region based on magnetic resonance image data, comprising:

acquiring magnetic resonance image data of a tissue region;

detecting the tissue region contained within the magnetic resonance image data;

acquiring information on an electrical property of the tissue region, the information being assigned to voxels of the tissue region;

simulating sensitivity profiles of radiofrequency (RF) receive coils to generate a simulated coil sensitivity map;

performing a pre-scan to acquire a calibrated coil sensitivity map;

comparing the simulated coil sensitivity map with the calibrated coil sensitivity map; and classifying the tissue region by analyzing the sensitivity profiles of the RF receive coils to detect changes in the electrical property of the tissue region, wherein the classifying is based upon the information on the electrical property of the tissue region and a match between the simulated coil sensitivity map and the calibrated coil sensitivity map.

16. The method according to claim 15, wherein the tissue region comprises a diagnostically-relevant tissue region that includes a cancerous tissue region or a tumorous tissue region.

17. The method according to claim 15, wherein the electrical property of the tissue region comprises a dielectric permittivity or a conductivity.

18. A method for classifying a tissue region based on magnetic resonance image data, comprising:

acquiring magnetic resonance image data of a tissue region;

detecting the tissue region contained within the magnetic resonance image data;

acquiring information on an electrical property of the tissue region, the information being assigned to voxels of the tissue region;

simulating a distribution of flip angles in the tissue region;

determining a measured distribution of flip angles based on the magnetic resonance image data;

comparing the simulated distribution of flip angles with the measured distribution of flip angles; and classifying the tissue region by analyzing B1+field maps to detect changes in the electrical property of the tissue region, wherein the classifying is based upon the information on the electrical property of the tissue region and a match between the simulated distribution of flip angles and the measured distribution of flip angles.

19. The method according to claim 18, wherein the tissue region comprises a diagnostically-relevant tissue region that includes a cancerous tissue region or a tumorous tissue region.

20. The method according to claim 18, wherein the electrical property of the tissue region comprises a dielectric permittivity or a conductivity.

* * * * *